United States Patent
Arnold et al.

(10) Patent No.: US 9,709,476 B2
(45) Date of Patent: Jul. 18, 2017

(54) SYSTEM AND METHOD FOR FINDING THE SIZE OF ONE OF MORE INDIVIDUAL PARTICLES, SUCH AS NANOPARTICLES FOR EXAMPLE, IN REAL TIME UTILIZING A MICROSPHERE'S WHISPERING GALLERY MODES ("WGMS")

(71) Applicants: Stephen Arnold, New York, NY (US); Ta Kang Keng, Rego Park, NY (US); Siyka Shopova, Staten Island, NY (US)

(72) Inventors: Stephen Arnold, New York, NY (US); Ta Kang Keng, Rego Park, NY (US); Siyka Shopova, Staten Island, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 14/858,342

(22) Filed: Sep. 18, 2015

(65) Prior Publication Data
US 2016/0084747 A1    Mar. 24, 2016

Related U.S. Application Data (60) Provisional application No. 62/052,224, filed on Sep. 18, 2014.

(51) Int. Cl.
*G01N 15/02* (2006.01)
*G01N 21/31* (2006.01)
*G01N 15/00* (2006.01)

(52) U.S. Cl.
CPC ........ *G01N 15/0205* (2013.01); *G01N 21/31* (2013.01); *G01N 2015/0038* (2013.01)

(58) Field of Classification Search
CPC .... G01N 15/02; G01N 15/0205; G01N 15/10; G01N 15/14; G01N 15/1434; G01N 2015/0038; G01N 2015/03; G01N 2015/1043; G01N 2015/105; G01N 2015/1087; G01N 2015/1493; G01N 21/31

See application file for complete search history.

(56) References Cited

U.S. PATENT DOCUMENTS

| | | | |
|---|---|---|---|
| 2004/0137478 A1* | 7/2004 | Arnold ................... | G01N 21/39 435/6.11 |
| 2011/0139970 A1* | 6/2011 | He ..................... | G01N 21/7746 250/227.18 |
| 2016/0030981 A1* | 2/2016 | Astratov ............... | B07C 5/3427 209/577 |

OTHER PUBLICATIONS

Keng, D., et al., "Whispering gallery micro-global positioning system for nanoparticle sizing in real time," Aug. 20, 2014, Applied Physics Letters, 105, pp. 071105-1 to 071105-4.*

(Continued)

*Primary Examiner* — Gordon J Stock, Jr.
(74) *Attorney, Agent, or Firm* — John C. Pokotylo; Straub & Pokotylo (57) ABSTRACT

Example systems and methods are provided to determine the size and/or mass of a particle, such as a nanoparticle for example, deterministically (i.e., non-statistically). At least two resonances of the same radial order, having the same angular momentum number l but different azimuthal numbers m (−l<m<l) are excited in a WGM resonator. The particle's latitude angle on the WGM resonator is located using a ratio of detected resonance wavelength shifts. Finally, at least one of (A) the particle's size, and (B) the particle's mass, is determined from the latitude angle of the particle.

10 Claims, 7 Drawing Sheets

(56) References Cited

OTHER PUBLICATIONS

Ozdemir, Sahin Kaya, et al., "Highly sensitive detection of nanoparticles with a self-referenced and self-heterodyned whispering-gallery Raman microlaser," Sep. 2, 2014, PNAS, www.pnas.org/cgi/doi/10.1073/pnas.1408283111, pp. E3836-E3844.*
Zhu, Jiangang, et al., "Single virus and nanoparticle size spectrometry by whispering-gallery-mode microcavities," Aug. 9, 2011, Optics Express, vol. 19, No. 17, pp. 1-12.*
Preston, Thomas C., et al., "Accurate and efficient determination of the radius, refractive index, and dispersion of weakly absorbing spherical particle using whispering gallery modes," Jul. 15, 2013, J. Opt. Soc. Am. B, vol. 30, No. 8, pp. 2113-2122.*
Kim, Woosung, et al., "Observation and characterization of mode splitting in microsphere resonators in aquatic environment," 2011, Applied Physics Letters 98, pp. 141106-1 to 141106-3.*
Yang, Lan, et al., "On-chip single nanoparticle detection using ultra-high-Q whispering gallery microresonator," 2010, Proc. of SPIE vol. 7682, pp. 76820B-1 to 76820B-11.*
Langbein, W., et al., "Modelling the response of whispering-gallery-mode optical resonators for biosensing applications," 2009, Proc. of SPIE vol. 7188, pp. 71880G-1 to 71880G-7.*

* cited by examiner

| Event | $\Delta\lambda_{340,340}$ (fm) | $\Delta\lambda_{340,330}$ (fm) | $|\xi_p|$ (deg) using Eq.6 | $a_p$ (nm) using Eq.7 | $\langle a_w \rangle \pm \sigma$ (nm) |
|---|---|---|---|---|---|
| 1. 600 sec | 800 ± 5 | 40 ± 5 | 0.49 ± 0.03 | 224.5 ± 0.3 | 228 ± 7 |
| 2. 874 sec | 670 ± 5 | 410 ± 5 | 1.72 ± 0.02 | 235.9 ± 0.2 | 228 ± 7 |
| 3. 2460 sec | 80 ± 7 | 360 ± 7 | 4.67 ± 0.26 | 217 ± 19 | 228 ± 7 |
| 4. 3860 sec | 150 ± 5 | 520 ± 5 | 4.10 ± 0.09 | 228.8 ± 4.2 | 228 ± 7 |

SYSTEM AND METHOD FOR FINDING THE SIZE OF ONE OF MORE INDIVIDUAL PARTICLES, SUCH AS NANOPARTICLES FOR EXAMPLE, IN REAL TIME UTILIZING A MICROSPHERE'S WHISPERING GALLERY MODES ("WGMS")

RELATED APPLICATION(S)

This application claims benefit to U.S. Provisional Application Ser. No. 62/052,224 (referred to as "the '224 provisional" and incorporated herein by reference), titled "METHOD FOR FINDING THE SIZE OF ONE OR MORE INDIVIDUAL NANOPARTICLES IN REAL TIME UTILIZING A MICROSPHERE'S WHISPERING GALLERY MODES ("WGMs")," filed on Sep. 18, 2014 and listing Stephen Arnold, David Keng and Siyka Shapova as the inventors. The scope of the present invention is not limited to any requirements of the specific embodiments described in '224 provisional.

GOVERNMENT RIGHTS

Research related to the described invention(s) has been supported by the National Science Foundation. The Federal Government may have certain rights to the described invention(s) under grant EECS 1303499.

BACKGROUND OF THE INVENTION

The need for precisely analyzing nanometer-sized particles (referred to as "nanoparticles" and including particles from about 1 nm to 1000 nm) is growing rapidly, as technology is trending towards minimizing the size of electronics and medical science is pushing diagnostics to the limit of recognizing individual biological molecules. A quantitative size/mass spectrometer that can work in solution, and work at single nanoparticle sensitivity, would allow for adding important information to body fluid analysis. Label-free sensors with this capability could identify viruses and exosomes not only by using bound antibodies, but also through their size. Furthermore, monitoring water resources for contamination with harmful nanoparticles, a waste product of the new technologies, is also an emerging need.

The sensitivity of whispering gallery mode ("WGM") resonances (referred to simply as "WGMs") of a WGM resonator to changes in its external environment has established WGM resonators as a leading platform for sensitive detection. (See, e.g., X. D. Fan, I. M. White, S. I. Shopova, H. Y. Zhu, J. D. Suter, and Y. Z. Sun, Anal, Chim. Acta 620, 8 (2008) (incorporated herein by reference).) Previous work by one of the present inventors pioneered a mechanism for detection based on WGMs. (See, e.g., S. Arnold, I. Teraoka, U.S. Pat. No. 7,491,491, "Detecting and/or Measuring a Substance Based On a Resonance Shift of Photons Orbiting Within a Microsphere" (incorporated herein by reference),) Plasmonic enhancement brought the sensitivity of a hybrid WGM-local surface plasmon resonator to the realm of detecting single nanoparticles/biomolecules. (See, e.g., S. Shopova, S. Arnold, R. Rajmangal, U.S. Pat. No. 8,493,560, 2013 "Plasmonic Enhancement of Whispering Gallery Mode Biosensors" (incorporated herein by reference).)

The present inventors were able to estimate the size of a particles adsorbed on a WGM resonator based on the largest change in the resonant frequency in a distribution of many events. However, such statistical techniques are non-deterministic and require many event samples.

U. S. Patent Application Publication No. 2010/0085573 (incorporated herein by reference), titled "Split Frequency Sensing Methods and Systems" discusses resonant sensors and molecule detection methods utilizing split frequency, but has some limitations, and is not used for determining the size (e.g., volume) and/or mass of a nanoparticle.

SUMMARY OF THE INVENTION

Figure 1:
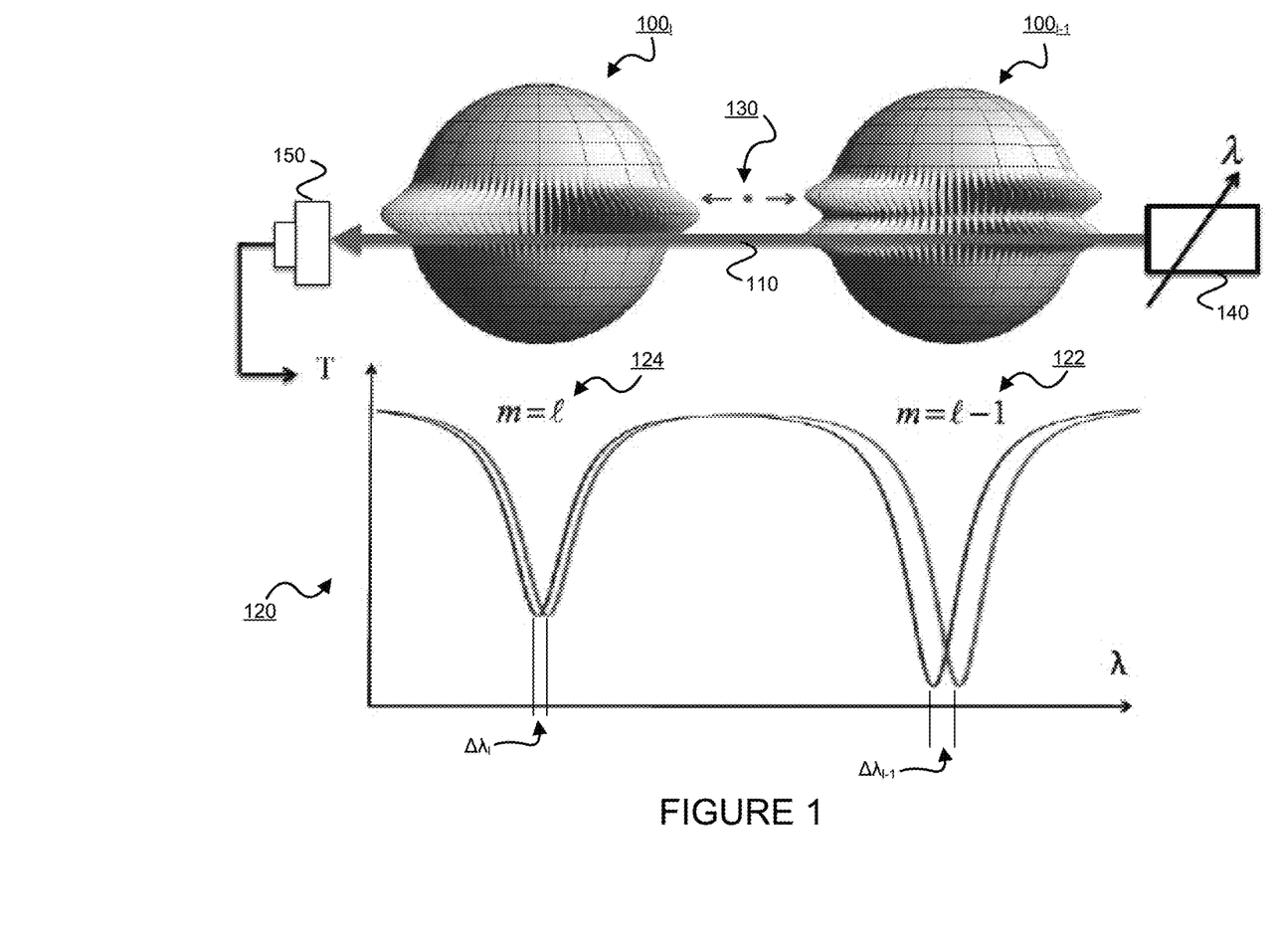
FIG. 1 illustrates polar modes intensities of a single, slightly prolate, micro-spheroid excited sequentially during a spectral laser scan through a guided wave in a tapered fiber positioned just below the equator, and its corresponding transmission spectrum.

The signal produced by a single particle (e.g., a nanoparticle) adsorbed on the surface is the shift in resonance wavelength $\Delta\lambda_r$ of a particular WGM resonance. The physical meaning of the relative shift, $\Delta\lambda_r/\lambda_r$, is the ratio of the energy required to polarize the nanoparticle to the energy in the cavity. (See, e.g., the article, S. Arnold, M. Khoshsima, I. Teraoka, S. Holler, and F. Vollmer, Opt. Lett. 28, 272 (2003) (incomorated herein by reference).) So the wavelength shift can be written as:

$$\Delta\lambda_r \cong \frac{\alpha_{ex}|E_0(r_p)|^2}{2\int\varepsilon_c|E_0(r_c)|^2\,dV}\lambda_r \qquad \text{Eq. 1}$$

where $r_p$ is the particle position, $r_c$ is a position within a cavity, $E_o$ is the field intensity, $\alpha_{ex}$ is the polarizability of the nanoparticle in excess of its environment (i.e. medium), and $\epsilon(r_c)$ is the permittivity of the cavity at position $r_c$. Equation 1 shows that the wavelength shift of each resonance is dependent on the electric field intensity for this particular resonance, at the particle position. In other words, the adsorption of the particle on the surface of the resonator will produce different shifts for different WGM resonances. FIG. 1 demonstrates this idea for a spheroidal resonator 100. More specifically, FIG. 1 illustrates polar modes intensities of a single slightly prolate micro-spheroid 100 excited sequentially during a spectral laser scan output by tunable laser 140 to a guided wave in a tapered fiber 110 positioned just below the equator, and its corresponding transmission spectrum 120 received by detector 150. The m=l−1 mode 122 on the right has a slightly longer resonance wavelength than the m=l mode 124 on the left. A nanoparticle (dot 130) adsorbed north of the equator has a larger overlap with the intensity of the m=l−1 mode 122 on the right. Consequently, the shift ($\Delta\lambda_{l-1}$) of this mode 122 is greater than that ($\Delta\lambda_l$) of mode 124. The ratio of the two shifts for the same microcavity can be used to locate the latitude of the nanoparticle 130. The polarizability and size/mass of the nanoparticle 130 can then be estimated from this location.

Example embodiments consistent with the present invention include a method for determining the size of a nanoparticle in one binding event (i.e., in real time) by utilizing two modes of different azimuthal symmetry of a WGM resonator. It involves the excitation of at least two resonances of the same radial order, having the same angular momentum number/but different azimuthal numbers m (−l<m<l) in a WGM resonator. The difference in the resonant shifts of two such modes comes from the electric field intensity dependence on the polar symmetry. (Recall FIG. 1, above.) The ratio of the resonance wavelength shifts ($\Delta\lambda_{l,l-1}/\Delta\lambda_{l,l}$) of these two modes is used to locate the nanoparticle's latitude. (See Equation 4, below.) Knowing the polar angle of the nanoparticle position allows its polarizability and size, and/or mass (if the density is known) to be calculated. (See Equation 5, below.)

DETAILED DESCRIPTION

Deterministic (Non-statistical) Technique for Determining Nanoparticle Mass and/or Size In the past, the edges of the longest wavelength shifts from many samples were used to determine the size of a nanoparticle on a WGM resonator. Here, the present inventors provide an analytical solution for the size of a nanoparticle adsorbed on a spheroidal microresonator.

When applied to a homogeneous microsphere (that is, a microsphere having a homogenous refractive index throughout), for which only two polar modes (m=l and m=l−1) are excited by the evanescent field of a tapered fiber or a prism, for a nanoparticle of radius a adsorbing on the surface, Eq.1 becomes:

$$\Delta\lambda_{l,m} \cong \frac{\alpha |Y_{l,m}(\xi_p)|^2 g(a/L)}{(n_s^2 - n_e^2)R^3}\lambda \qquad \text{Eq. 2}$$

where α is the polarizability of the nanoparticle, g(a/L) is a geometric factor (See, e.g., D. Keng, X. Tan, and S. Arnold, Appl. Phys. Lett. 105, 071105 (2014) (incorporated herein by reference).), λ is the resonant wavelength of the microsphere, a is the nanoparticle's radius, $$\alpha = \frac{\alpha_{ex}}{\varepsilon_0} = 4\pi n_e^2 \frac{n_p^2 - n_e^2}{n_p^2 + 2n_e^2}a^3$$

is the "geometric" polarizability that is proportional to the volume of the nanoparticle ($a^3$), $n_s$, $n_e$ and $n_p$ are the refractive indices of the microsphere, environment, and nanoparticle, respectively, R is the microsphere radius, L is the characteristic evanescent intensity length obtained from Mie theory, $Y_{l,m}(\xi_p)$ is the vector spherical harmonic function determined by the two quantum numbers, l and m, and $\xi_p$ is the latitude of the adsorbed nanoparticle. The form factor g corrects the simple point dipole theory (Equation 1) for a nanoparticle that is extended in size (a~L). (See, e.g., the article, D. Keng, X. Tan, and S. Arnold, Appl. Phys. Lett. 105, 071105 (2014) (incorporated herein by reference)) The form factor has a simple limiting property, for a<<L, g≅1.

The ratio of wavelength shifts of the m=l−1 to the m=l modes gives the square of the ratio of the vector spherical harmonics, considering that the shifts are very small in comparison to the resonant wavelengths and that l is a large number (determined from the radius of the microsphere). The ratio of the spherical harmonics is a simple function of the polar angle $\xi_p$:

$$\frac{\Delta\lambda_{l,l-1}}{\Delta\lambda_l} \cong \left|\frac{Y_{l,l-1}(\xi_p)}{Y_{l,l}(\xi_p)}\right|^2 = 2l[\tan(\xi_p)]^2 + 2l \qquad \text{Eq.3}$$

with the latitude of the bound particle $\xi_p$ determined from:

$$\xi_p = \arctan\left(\sqrt{\frac{l}{2l}\left(\frac{\Delta\lambda_{l,l-1}}{\Delta\lambda_{l,l}} - \frac{2}{l}\right)}\right) \qquad \text{Eq. 4}$$

This expression is exact at the equator, wherein $\xi_p$ is zero (0). The error due to approximation is less than 1.15% for any other angle.

The radius a of the nanoparticle can be determined by re-expressing Equation 2 as:

$$a^3 g(a/L) \cong \frac{(n_s^2 - n_e^2)R^3}{|Y_{l,l}(\xi_p)|^2 4\pi n_e^2 \frac{n_p^2 - n_e^2}{n_p^2 + n_e^2}} \frac{\Delta\lambda_{l,l}}{\lambda} \qquad \text{Eq.5}$$

Note that Equation 3 does not require assumption of "small angle." That is, it does not rely on an assumption that the nanoparticle is close to the equator of the microsphere. In the limit of form factor (that is, g(a/L)~1), Equation 5 gives the size of a spherical particle smaller than the evanescent length L. Given the volume of the nanoparticle, its mass can be derived if its density is known.

Example System

Figure 2:
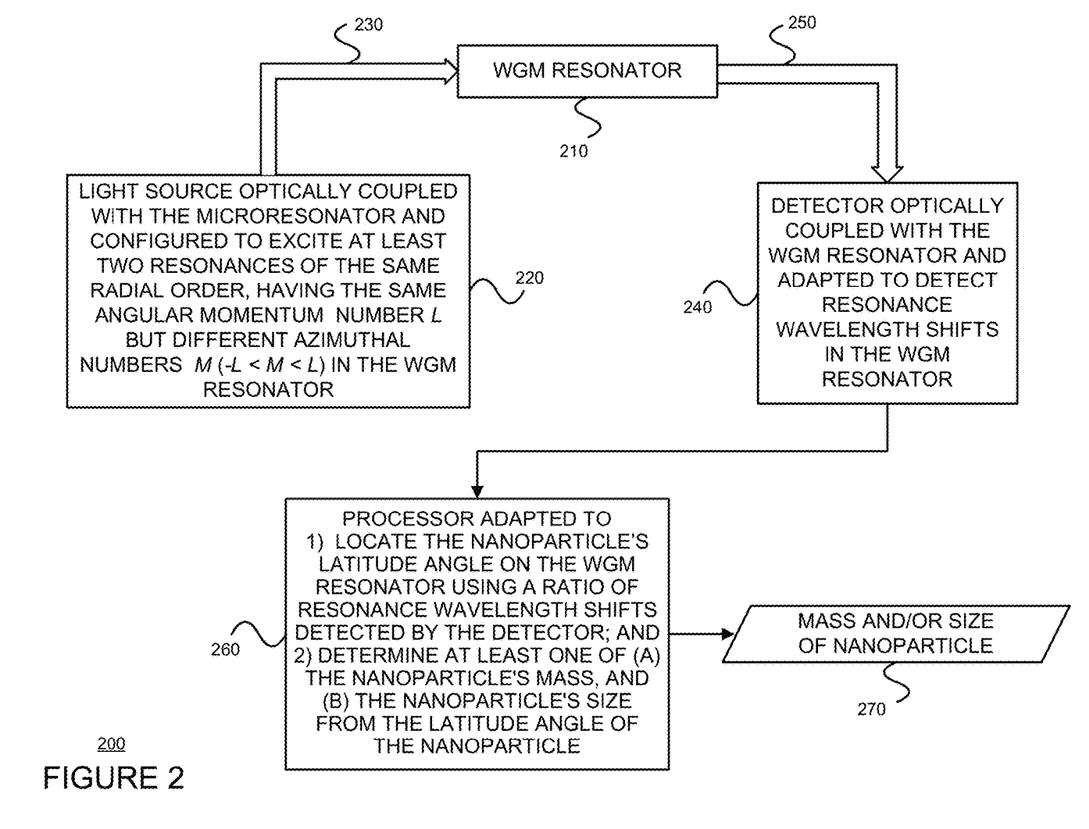
FIG. 2 is a block diagram of an example system for determining a mass and/or size of a nanoparticle, consistent with the present invention.

FIG. 2 is a block diagram of an example system 200 for determining a mass and/or size of a nanoparticle, consistent with the present invention. The system 200 includes a WGM resonator 210 optically coupled with a light source 220 via feed (e.g., optical fiber) 230 and optically coupled with a detector 240 via pickup (e.g., optical fiber) 250. The output of the detector 240 is provided to a processor 260.

In some example embodiments consistent with the present invention, the WGM resonator 210 is a passive resonator, and light coupled from the light source 220 produces at least two azimuthal modes. In other example embodiments consistent with the present invention, the WGM resonator 210 is an active resonator, the light source 220 produces Raman gain in the material of the WGM resonator 210, and there are at least two azimuthal modes of the WGM resonator 210 in the Raman spectral range. The WGM resonator 210 may be, for example, one of (A) a spheroid, (B) rolled cylindrical, or (C) a toroid. The WGM resonator 210 may be formed of silica, amorphous sapphire glass, silicon, silicon nitride, silicon oxynitride, gallium nitride (GaN), gallium arsenide (GaAs), indium arsenide (InAs), etc. In at least some exemplary embodiments consistent with the present invention, the microresonator may have a diameter of as low as 4 μm for high refractive index (e.g., n=1.9) materials, and as low as 40 μm for silica, though resonators having other diameters (generally, about 10 μm to 200 μm, depending on the index of refraction of the resonator) may be used.

The light source 220 is configured to excite at least two resonances of the same radial order, having the same angular momentum number L but different azimuthal numbers M (wherein $-L<M<L$) in the WGM resonator 210. In some example embodiments consistent with the present invention, the light source 220 is a laser having a wavelength of 1062 nm, and a laser power of between 100 μW and 3 mW, Naturally, other laser wavelengths and drive powers may be used.

The detector 240 is adapted to detect resonance wavelength shifts in the WGM resonator 210.

Assuming a nanoparticle is provided (e.g., adsorbed) on the WGM resonator 210, the processor 260 is adapted to (1) locate the nanoparticle's latitude angle on the WGM resonator 210 using a ratio of resonance wavelength shifts detected by the detector 240, and (2) determine at least one of (A) the nanoparticle's size and/or (B) the nanoparticle's mass 270 from the latitude angle of the nanoparticle. The processor 260 may be a microprocessor, executing program instructions. Such program instructions may be stored, for example, on a non-transitory computer readable medium and/or received from a remote source. The processor 260 may include integrated circuits, and may be a general purpose computer, or an application specific integrated circuit ("ASIC"). The processor 260 may be embodied as hardware, software, or both.

Example Method

Figure 3:
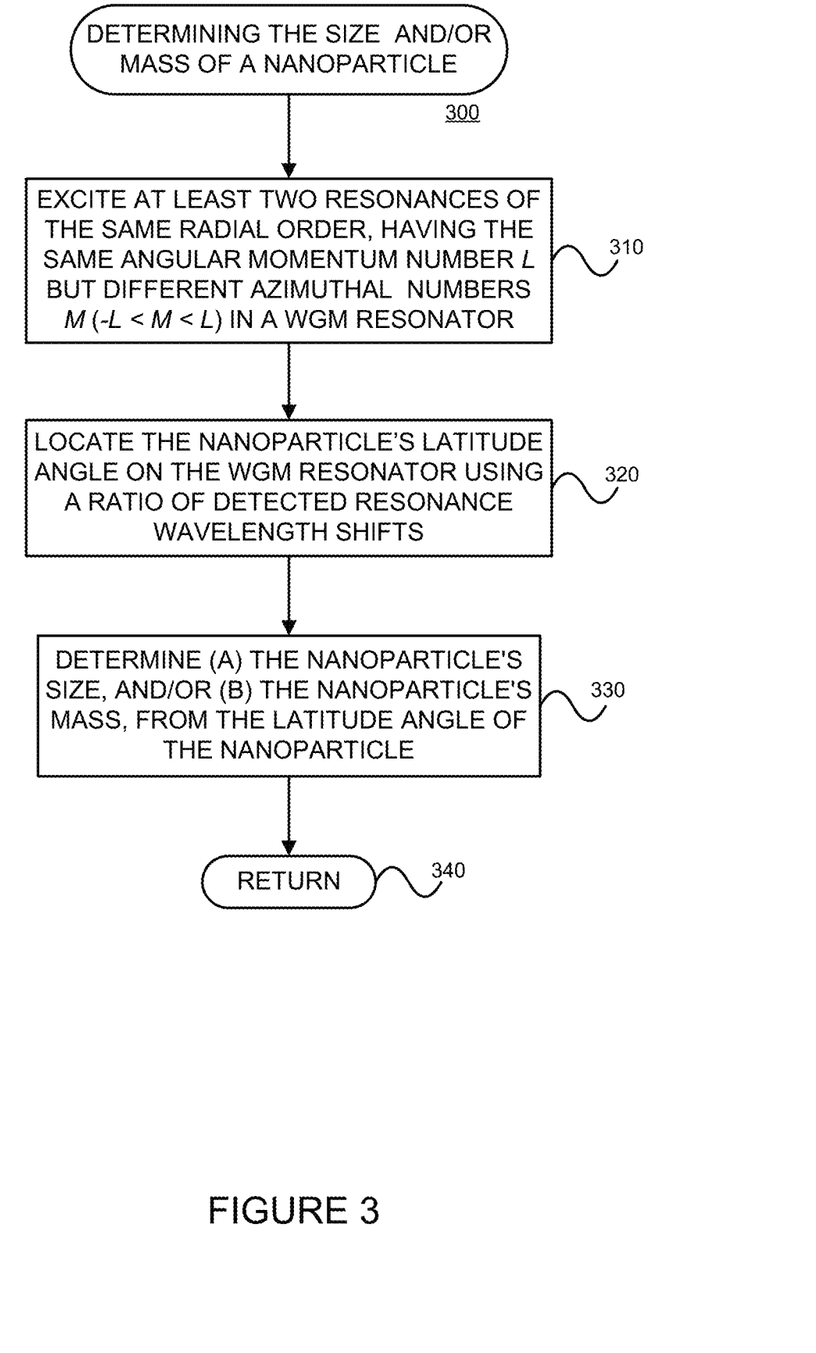
FIG. 3 is a flow chart of an example method for determining a mass and/or size of a nanoparticle, consistent with the present invention.

FIG. 3 is a flow chart of an example method 300 for determining a size and/or mass of a nanoparticle, consistent with the present invention. First, at least two resonances of the same radial order, having the same angular momentum number/but different azimuthal numbers m ($-l<m<l$) are excited in a WGM resonator (e.g., by light source 220 of FIG. 2). The nanoparticle's latitude angle on the WGM resonator is then located using a ratio of detected resonance wavelength shift (e.g., by processor 260 of FIG. 2). (Recall, e.g., Equation 4 above.) Finally, at least one of (A) the nanoparticle's size, and (B) the nanoparticle's mass is determined from the latitude angle of the nanoparticle (e.g., by the processor 260 of FIG. 2.). (Recall, e.g., Equation 5 above.)

Experimental Results and Discussion

Figure 4:
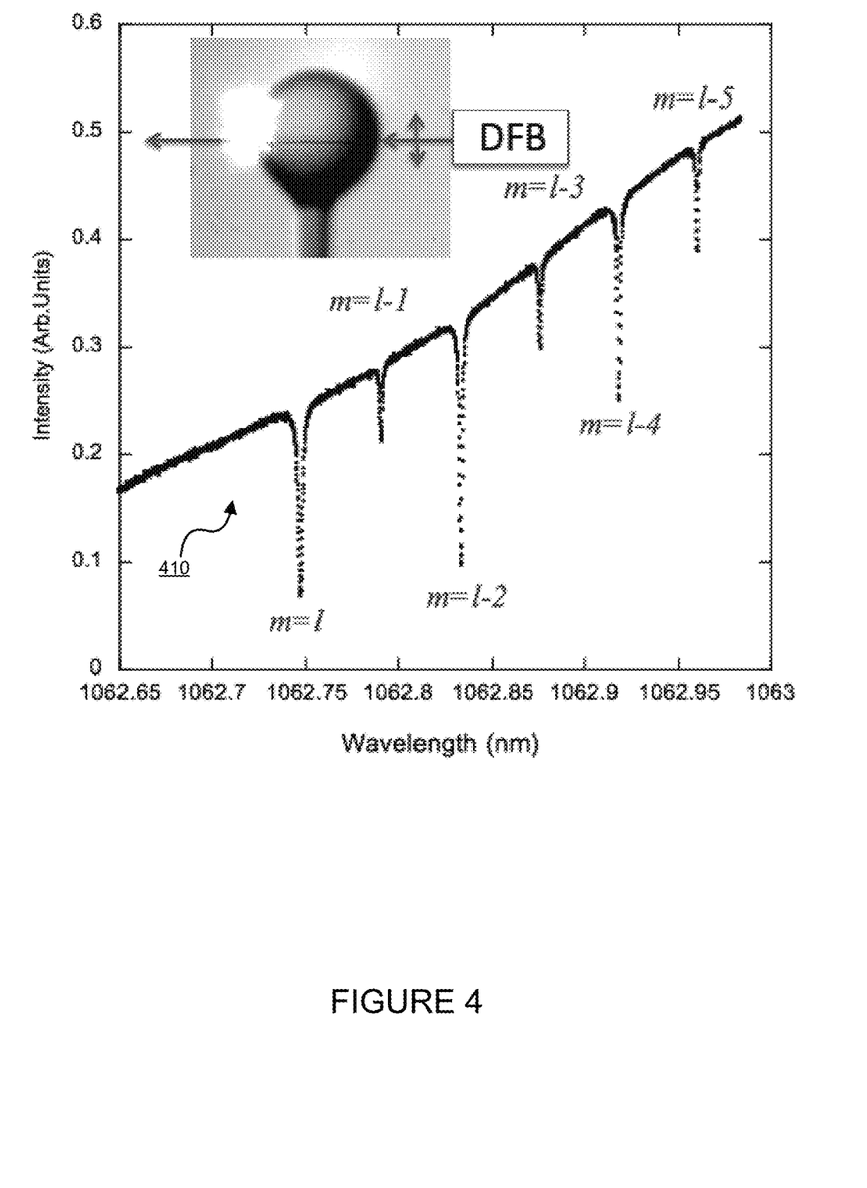
FIG. 4 illustrates the spectrum of a slightly prolate microcavity immersed in 30 mM NaCl solution and excited by tapered fiber coupling just below the equator (as seen in the inset).

To test the foregoing "micro-latitude locator" method, the present inventors formed micro-spheroids by using $CO_2$ laser melting at the end of a tapered silica optical fiber. (See the inset of FIG. 4.) Shape analysis of the images revealed that the formed resonators were slightly prolate or oblate (eccentricity <3%). These silica micro-spheroids were then installed into a custom microfluidic system (See, e.g., the article S. Arnold, R. Ramjit, D. Keng, V. Kolchenko, and I. Teraoka, Faraday Disc. 137, 65 (2008) (incorporated herein by reference)), where they were coupled to a tapered optical fiber. In the inset of FIG. 4, the fiber is beneath the spheroid. A typical under-coupled spectrum 410 taken through the coupling fiber is shown in FIG. 4. More specifically, FIG. 4 illustrates the spectrum of a slightly prolate microcavity immersed in 30 mM NaCl solution and excited by tapered fiber coupling just below the equator as seen in the inset. The equatorial radius was 41 microns. From Mie theory l=340 with all modes having TE polarization. A distributed feedback ("DFB") laser was scanned with a saw tooth drive having a period of 100 msec.

All of the resonances were excited with a 1063 nm tunable DFB laser polarized along a meridian (Transverse Electric (TE) polarization). The laser was current tuned with a saw tooth wave that accounts for the rising backbone of the spectrum. It should be noted that the resonance dip on the left has no neighbor at shorter wavelength. This is the signature of the m=l equatorial mode of a prolate spheroid; the m=l mode has the shortest wavelength. (See, e.g., the article, G. Lin, B. Qian, F. Orucevic, Y. Candela, J. B. Jager, Z. Cai, V. Lefevre-Segun, and J. Hare, Opt. Lett. 35, 583 (2010) (incorporated herein by reference)) To the right of this mode (longer wavelength) is the m=l-1 mode, which is narrower, with a smaller dip. Note that the m=l-2 mode is of similar depth to the m=l mode and the m=l-3 mode to longer wavelength looks similar in depth to the m=l-1 mode. This sequence of deep-shallow-deep-shallow dips in FIG. 4 is a consequence of the overlap between the fiber field and the polar symmetries of the WGMs. Whereas the m=l mode is symmetric in latitude about the equator, as is the fiber field, the m=l-1 mode is asymmetric. Exciting the asymmetric WGM mode requires that the centerline of the exciting fiber be slightly above or below the equator. The fiber is placed in contact with the resonator to reduce mechanical vibration noise. This results in a red shift and broadening of the resonances. Upon coupling, neither the m=l resonance, nor the m=l-1 resonance, had quality factors ("Qs") larger than $2 \times 10^5$.

The validity of the "micro-latitude locator" method was tested by injecting nanoparticles (polystyrene $<a_m> \pm \sigma = 228 \pm 7$ nm from Polysciences) at a 20 fM concentration into our microfluidic system in the presence of the resonator depicted in FIG. 4. The solution had a 30 mM NaCl concentration to promote binding to the silica surface by decreasing the Debye length associated with ionized silanol groups. (See, e.g., the article, S. Arnold, D. Keng, S. I. Shopova, S. Holler, W. Zurawsky, and F. Vollmer, Optics Express 17, 6230 (2009) (incorporated herein by reference).)

Figure 5A:
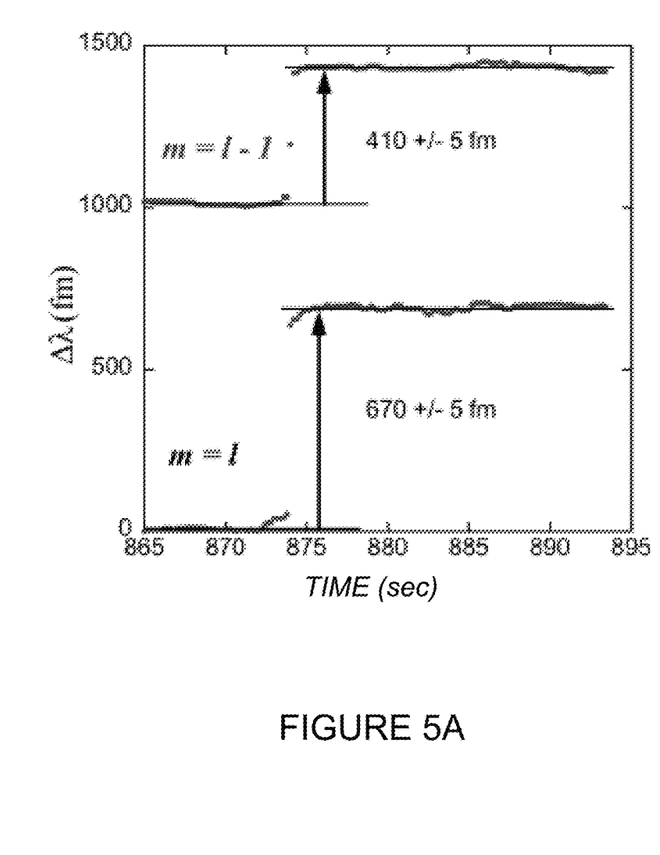
FIGS. 5A and 5B illustrate two event recordings of the m=l, m=l−1, modes for signaling the binding of two polystyrene nanospheres to the micro-spheroid in FIG. 4.
Figure 5B:
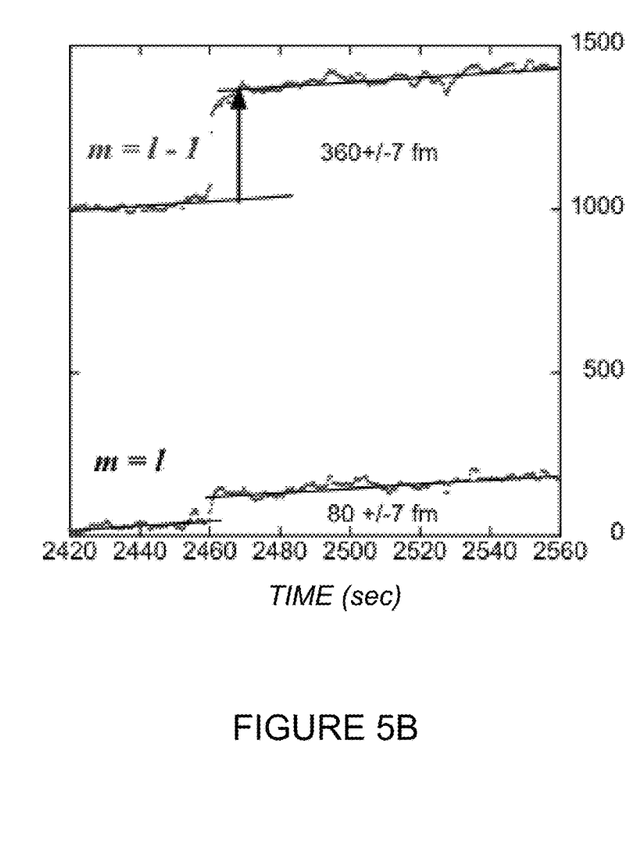

FIGS. 5A and 5B show data for two typical events. More specifically, FIGS. 5A and 5B show two event recordings of the m=l, m=l-1, modes for signaling the binding of two polystyrene nanospheres to the microspheroid in FIG. 4. For each event, an offset of 1000 fm between the m=l and m=l-1 modes was chosen for clarity. The particles used are reported by the manufacturer (Polysciences) as having an ensemble radius $<a_m> = 228$ nm with a standard deviation of 7 nm. For the binding event near 874 seconds in FIG. 5A, $\Delta\lambda_{l,l} > \Delta\lambda_{l,l-1}$. The opposite is true for the binding event on the right near 2460 sec in FIG. 5B. Although the m=l event in FIG. 5A demonstrates a shift of 700% greater than that in FIG. 5B, the differences in the radii arrived at from equations 4 and 5 is less than 8%. These results, as well as others, are listed in the table of FIG. 6.

The event in FIG. 5A appeared 874 sec following the injection with a wavelength shift of 680±5 fm for the m=l mode and 410±5 fm for the m=l-1 mode. For the event in FIG. 5B which occurred 2460 sec after injection the smaller shift occurred for the m=l mode; 80±7fm as compared with 360±7 fm for the m=l-1 mode. For the former case the latitude at which the nanosphere attached from Equation 4 in degrees is 1.72±0.02. After numerically solving Equation 5, the radius of this nanosphere is determined to be 235.8±0.2 nm. The latitude for the nanoparticle attachment in FIG. 5B is 4.65±0.26 degrees, and the radius from Equation 5 is 216±19 nm. Compared with the ensemble average from hydrosol manufacturer $<a_m> \pm \sigma = 228 \pm 7$ nm, both results from the example "micro-latitude locator" method overlap. Table 1 of FIG. 6 shows the analysis of four recorded events.

Figure 6:
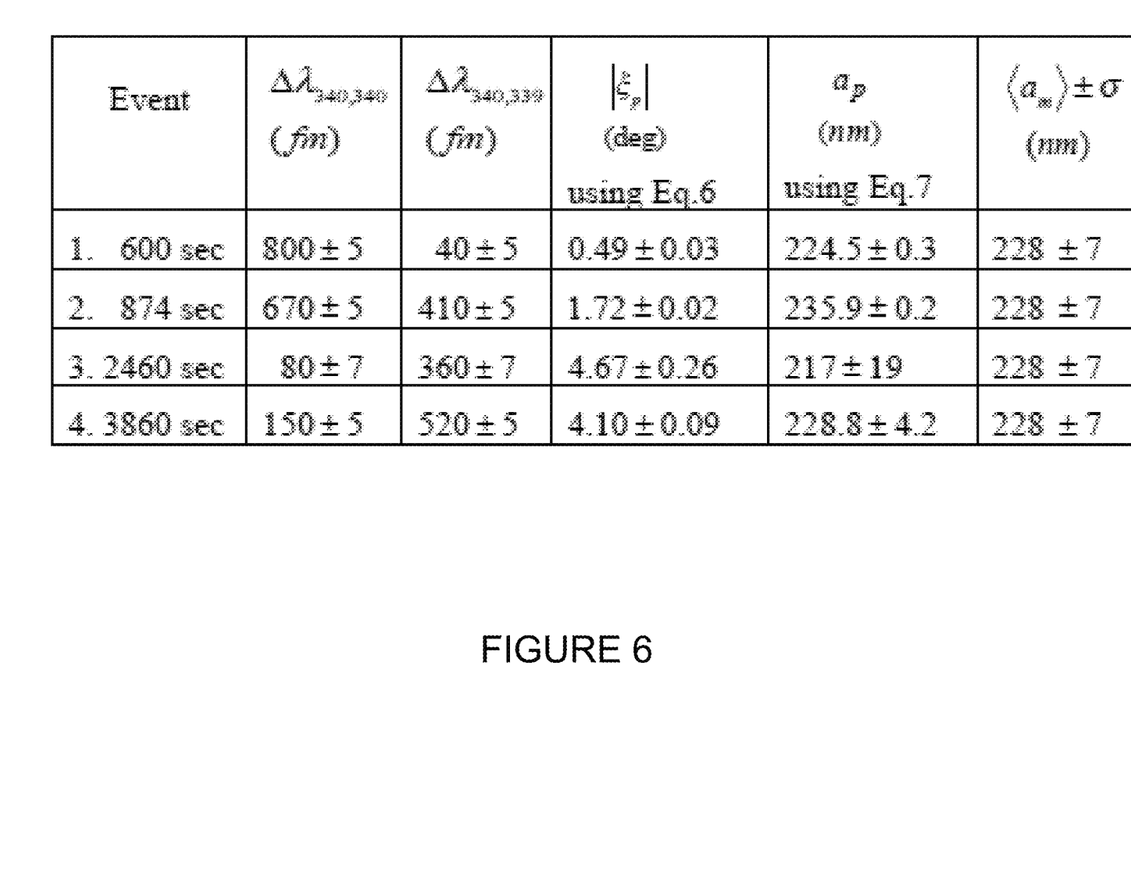
FIG. 6 is a table illustrating four events following the injection of polystyrene nanospheres from a manufactured hydrosol (Polysciences) having an ensemble mean radius $<a_m>=228$ nm with a standard deviation of $\sigma=7$ mm

More specifically, the table of FIG. 6 illustrates data from four events following the injection of polystyrene ("PS") nanospheres from a manufactured hydrosol (Polysciences)

having a ensemble mean radius $\langle a_m \rangle = 228$ nm with a standard deviation of $\sigma = 7$ nm. The microcavity was the one in FIG. 4. Each of the particle radii $a_p$ in the 5th column are determined only from the data for the associated event using Equations 4 and 5. The refractive indices $n_s$, $n_e$, and $n_p$ were taken as 1.449, 1.326, and 1.572, respectively.

In all cases, the "micro-latitude locator" results in the column marked $a_p$ including measurement uncertainties overlap the manufacturer's ensemble measurements.

One important application of the "micro-latitude locator" method is expected to be measuring the size distribution in a heterogeneous solution, in which each binding event counts. To test the suitability of the "micro-latitude locator" method for such an application, the present inventors added 178 nm polystyrene ("PS") beads to 228 nm PS beads used previously.

Figure 7:
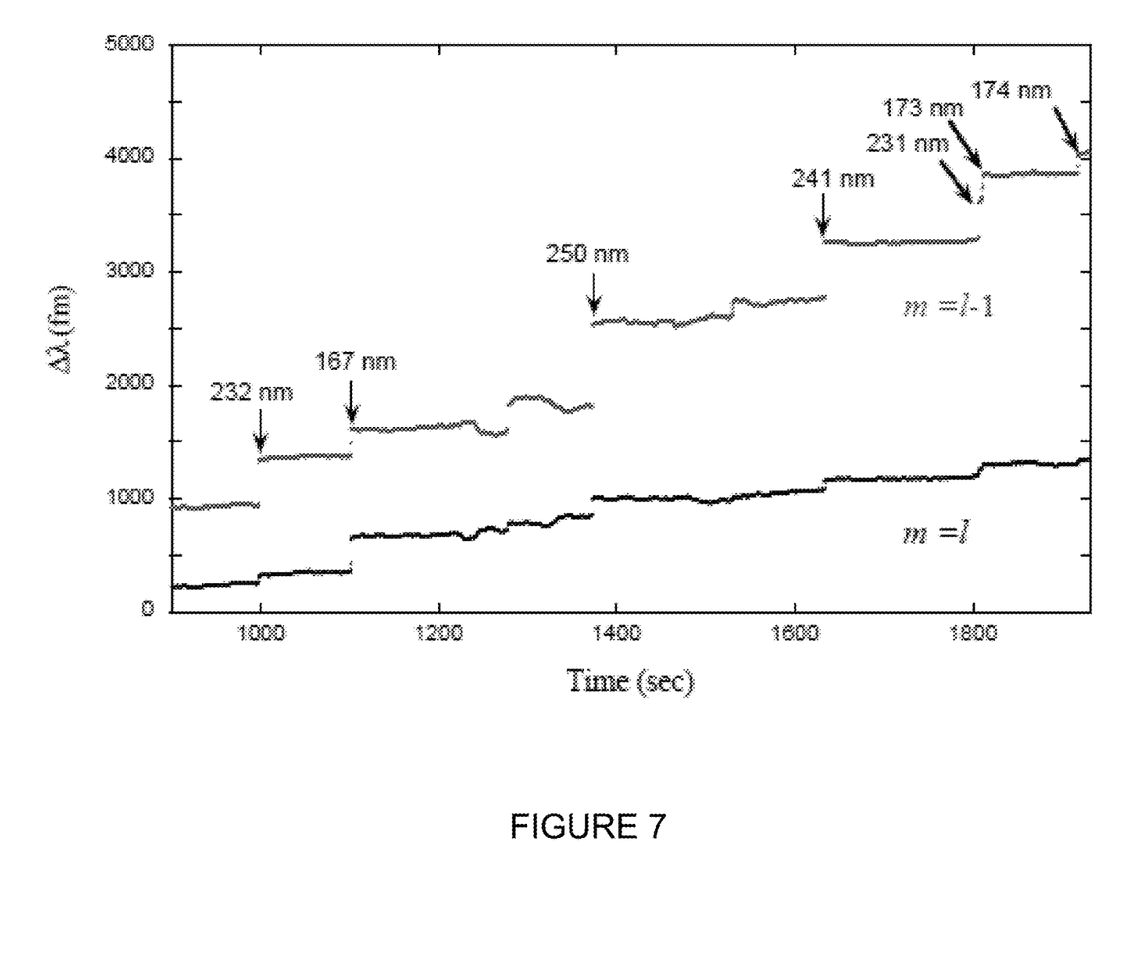
FIG. 7 illustrates experimental binding curves on a 41 μm radius slightly prolate spheroid recorded for the m=l and m=l−1 modes.

FIG. 7 shows the binding curves recorded for the m=l and m=l-1 modes. The latitude locator Equation 4, combined with Equation 5 easily identified two particle ranges, 231 to 250 nm, and 167 to 174 nm More specifically, in FIG. 7, experimental binding curves on a 41 μm radius slightly prolate spheroid were recorded for the m=l and m=l-1 modes. The solution contained PS nanospheres (mixture) having manufactured ensemble radii of 178 ±7 and 228±7. The numbers at the beginning of each binding event is the computed radius for that event based on Equations 4 and 5.

The last experiment clearly shows that the "micro-latitude locator" method is capable of real time sizing of binding particles to a WGM resonator surface. Although the foregoing analytic solution and experimental verification were done for a spheroidal resonator, the "micro-latitude locator" method can be generalized to resonators of different shapes, such as, for example cylindrical, or toroidal. Similar m modes have been identified in rolled up cylinders (See, e.g., the article, S. Li, L. Ma, H. Zhen, M. R. Jorgensen, S. Kiravittaya, and O. G. Schmidt, Appl. Phys. Lett. 101, 231106 (2012) (incorporated herein by referenec).) and micro-toroids (See, e.g., the article S. Arnold, D. Keng, S. I. Shopova, S. Holler, W. Zurawsky, and F. Vollmer, Optics Express 17, 6230 (2009) (incorporated herein by reference)), However multiple m modes have not been used previously for precise nanoparticle sizing with these designs.

CONCLUSIONS

By providing a simple relation between the size of any adsorbed nanoparticle and the reactive response of the WGM resonator, example embodiments consistent with the present invention extend the capabilities of WGM-based sensing to a real-time size spectrometry. Some example embodiments consistent with the present invention permit receptor-free detection, and/or measurement of target particle size (and/or mass). Finally, rather than providing a statistical solution based on the longest wavelength shift from many samples, example embodiments consistent with the present invention provide a deterministic and analytic solution. Although example embodiments were discussed with reference to nanoparticles (which can range from about 1 nm to 1000 nm, and preferably from about 15 nm-250 nm), such example embodiments will likely be effective for measuring the size and/or mass of larger and/or smaller particles.

What is claimed is:

1. A method for determining the size of a particle, the method comprising:
   a) exciting at least two resonances of the same radial order, having the same angular momentum number l but different azimuthal numbers m ($-l \leq m \leq l$) in a WGM resonator on which the particle has been adsorbed;
   b) locating the particle's latitude angle on the WGM resonator using a ratio of detected resonance wavelength shifts; and
   c) determining at least one of (A) the particle's size, and (B) the particle's mass, from the latitude angle of the particle.

2. The method of claim 1 wherein the act of locating the particle's latitude angle on the WGM resonator using a ratio of detected resonance wavelength shifts includes determining:

$$\xi_p = \arctan\left(\sqrt{\frac{l}{2l}\left(\frac{\Delta\lambda_{l,l-1}}{\Delta\lambda_{l,l}} - \frac{2}{l}\right)}\right)$$

where $\lambda_l$ and $\lambda_{l-1}$ are resonance wavelengths at polar modes of the WGM resonator.

3. The method of claim 1 wherein the act of determining at least one of (A) the particle's mass, and (B) the particle's size from a polar angle of the particle position includes determining:

$$a^3 g(a/L) \cong \frac{(n_s^2 - n_e^2)R^3}{|Y_{l,l}(\xi_p)|^2 4\pi n_e^2 \frac{n_p^2 - n_e^2}{n_p^2 + n_e^2}} \frac{\Delta\lambda_{l,l}}{\lambda}$$

where $\lambda$ is the resonant wavelength of the microsphere, a is the particle's radius, $a^3$ is the particle's volume, $$\alpha = \frac{\alpha_{ex}}{\varepsilon_0} = 4\pi n_e^2 \frac{n_p^2 - n_e^2}{n_p^2 + 2n_e^2} a^3$$

is the "geometric" polarizability that is proportional to the volume of the particle, $n_s$, $n_e$ and $n_p$ are the refractive indices of the WGM resonator, its environment, and particle, respectively, R is the WGM resonator's radius, L is the characteristic evanescent intensity length obtained from Mie theory, $Y_{l,m}(\xi_p)$ is the vector spherical harmonic function determined by the two quantum numbers, l and m, and $\xi_p$ is the latitude of the adsorbed particle.

4. The method of claim 1 wherein the WGM resonator is one of (A) a spheroid, (B) rolled cylindrical, or (C) a toroid.

5. The method of claim 1 wherein the particle is a nanoparticle, having a radius between 1 nm and 1000 nm.

6. Apparatus for determining the size of a particle, the apparatus comprising:
   a) a WGM resonator;
   b) a light source optically coupled with the WGM resonator and configured to excite at least two resonances of the same radial order, having the same angular momentum number l but different azimuthal numbers m ($-l \leq m \leq l$) in the WGM resonator;
   c) a detector optically coupled with the WGM resonator and adapted to detect resonance wavelength shifts in the WGM resonator on which the particle has been adsorbed; and d) a processor configured to
   1) locate the particle's latitude angle on the WGM resonator using a ratio of resonance wavelength shifts detected by the detector; and
   2) determine at least one of (A) the particle's mass, and (B) the particle's size from the latitude angle of the particle.

7. The apparatus of claim 6 wherein the WGM resonator is a passive resonator, and wherein light coupled from the light source produces at least two azimuthal modes.

8. The apparatus of claim 6 wherein the WGM resonator is an active resonator, and wherein the light source produces Raman gain in the material of the WGM resonator, and wherein there are at least two azimuthal modes of the WGM resonator in the Raman spectral range.

9. The apparatus of claim 6 wherein the WGM resonator is one of (A) a spheroid, (B) rolled cylindrical, or (C) a toroid.

10. The apparatus of claim 6 wherein the particle is a nanoparticle, having a radius between 1 nm and 1000 nm.

* * * * *

UNITED STATES PATENT AND TRADEMARK OFFICE
CERTIFICATE OF CORRECTION

PATENT NO. : 9,709,476 B2
APPLICATION NO. : 14/858342
DATED : July 18, 2017
INVENTOR(S) : Stephen Arnold, Ta Kang Keng and Siyka Shopova It is certified that error appears in the above-identified patent and that said Letters Patent is hereby corrected as shown below:

In the Specification

Column 1, Lines 24-27, should be corrected by replacing:
"Research related to the described invention(s) has been supported by the National Science Foundation. The Federal Government may have certain rights to the described invention(s) under grant EECS 1303499."
With:
-- This invention was made with government support under grant number EECS1303499 awarded by the National Science Foundation. The government has certain rights in the invention. --

Signed and Sealed this
Twentieth Day of December, 2022

Katherine Kelly Vidal
*Director of the United States Patent and Trademark Office*